United States Patent [19]
Schrock et al.

[11] Patent Number: 5,087,710
[45] Date of Patent: Feb. 11, 1992

[54] HOMOGENEOUS RHENIUM CATALYSTS FOR METATHESIS OF OLEFINS

[75] Inventors: Richard R. Schrock, Winchester, Mass.; Robert Toreki, Morrisville, Pa.

[73] Assignee: Massachusetts Institute of Technology, Cambridge, Mass.

[21] Appl. No.: 461,040

[22] Filed: Jan. 4, 1990

[51] Int. Cl.$^5$ .............................................. C07F 13/00
[52] U.S. Cl. ..................................... 556/46; 556/10; 556/12; 556/21; 556/22; 540/2; 502/152; 502/155; 502/156
[58] Field of Search ................. 502/152, 155, 156; 556/10, 12, 21, 46; 546/2

[56] References Cited

U.S. PATENT DOCUMENTS 4,681,956 7/1987 Schrock ................................ 556/12
4,727,215 2/1988 Schrock ................................ 585/645

FOREIGN PATENT DOCUMENTS 057736 8/1982 European Pat. Off. .
191675 8/1986 European Pat. Off. .
218138 4/1987 European Pat. Off. .
2525224 10/1983 France .

OTHER PUBLICATIONS

Edwards, D. S. et al., *Organometallics*, 2:1505–1513, (1983).
Edwards, D. S., Ph.D. Thesis, Massachusetts Institute of Technology, May 1983, (Catalogued at M.I.T. on 1/4/85).
Grubbs, R. H. in *Comprehensive Organometallic Chemistry*, (1982), Wilkinson, G. et al., (Eds.), vol. 8, Pergamon: New York, pp. 499–551.
Horton, A. D., et al., *Organometallics*, 6:893–894, (1987).
Leconte, M. et al. in *Reaction of Coordinated Ligands*, (1986), Braterman, P. R. (Ed.), Plenum: New York, pp. 371–420.
Murdzek, J. S. and R. R. Schrock, *Organometalics*, 6:1373–1374, (1987).
Bazan, G. et al., *Polymer Commun.*, 30:258–260, (1989).
Schrock, R. R., et al., *J. Am. Chem. Soc.*, 110:1423–1435, (1988).
Feldman, J. et al. in *Advances in Metal Carbene Chemistry*, Schubert, U. (Ed.), Kluwer Academic Publishers, Boston, (1989), pp. 323–346.
Schrock, R. R. et al., *Macromolecules*, 20:1169–1172, (1987).
Ginsburg, E. G. et al., *J. Am. Chem. Soc.*, 111:7621–7622, (1989).
Swager, T. M. and R. H. Grubbs, *J. Am. Chem. Soc.*, 111:4413–4422, (1989).
Knoll, K. and R. R. Schrock, *J. Am. Chem. Soc.*, 111:7989–8004, (1989).
Horton, A. D. and R. R. Schrock, *Polyhedron*, 7:1841–1853, (1988).
Schlund, R. et al., *J. Am. Chem. Soc.*, III:8004, (1989).
Cai, S. et al., *J. Am. Chem. Commun.*, 1489, (1988).
International Search Report for PCT/US91/00090.

*Primary Examiner*—Asok Pal
*Assistant Examiner*—E. D. Irzinski
*Attorney, Agent, or Firm*—Hamilton, Brook, Smith & Reynolds

[57] ABSTRACT

The invention pertains to rhenium (VII) compounds which are catalysts for metathesis of ordinary olefins (hydrocarbons) and functionalized olefins in a homogeneous phase and to methods of synthesizing these compounds. The rhenium compounds comprise a rhenium (VII) atom centrally linked to an alkylidene ligand, an alkylidyne ligand, and two other ligands of which at least one ligand is sufficiently electron withdrawing to render the rhenium atom significantly active for metathesis.

17 Claims, No Drawings

HOMOGENEOUS RHENIUM CATALYSTS FOR METATHESIS OF OLEFINS

GOVERNMENT SUPPORT

The invention described herein was supported by Grant No. CHE88-22508, from the National Science Foundation. The Government has certain rights in the invention.

BACKGROUND OF THE INVENTION

Metathesis of olefins is a process that is defined as the redistribution of alkylidene moieties in a mixture of olefins to yield other olefins. A simple example of olefin metathesis is shown in equation I.

$$2RHC=CHR' \rightleftharpoons R'HC=CHR' + RHC=CHR \qquad Eq. \ 1$$

The reaction proceeds by addition of an olefin to a catalyst having a metal-carbon double bond. Three of the most active metals used in classical olefin metathesis are molybdenum, tungsten and rhenium. (Ivin, K. J., *Olefin Metathesis*, Academic Press, London, 1983; Grubbs, R. H. in *Comprehensive Organometallic Chemistry*, Wilkinson, G. et al. (Eds.), Vol. 8, Pergamon: N.Y. (1982); Dragutan, V. et al., *Olefin Metathesis and Ring-Opening Polymerization of Cyclo-Olefins*, 2nd Ed., Wiley-Interscience: New York (1985); Leconte, M. et al. in *Reactions of Coordinated Ligands*, Braterman. P. R. (Ed.). Plenum: N.Y. (1986).)

Examples of molybenum (VI) alkylidene complexes (Murdzek, J. S. and R. R. Schrock, *Organometallics* 6:1373 (1987); Bazan. G. et al., *Polymer Commun.* 30:258 (1989)) and tungsten (VI) alkylidene complexes have been previously described (Schrock. R. R. et al., *J. Am. Chem. Soc.* 110:1423 (1988); Feldman, J. et al. in *Advances in Metal Carbene Chemistry*, Schubert, U. (Ed.). Kluwer Academic Publishers. Boston: 1989, page 323; Schrock. R. R. et al., *Macromolecules* 20:1169 (1987); Ginsburg, E. J. et al., *J. Am. Chem. Soc.* 111:7621 (1989); Swager, T. M. et al., *J. Am. Chem. Soc.* 111:4413 (1989); Knoll. K. and R. R. Schrock. *J. Am. Chem. Soc.* 111:7989 (1989); Schlund, R. et al., *J. Am. Chem. Soc.* 111:8004 (1989)). Several of these compounds have been shown to catalyze the metathesis of olefins with an activity that can be controlled through the choice of the alkoxide ligand. For example. tungsten and molybdenum catalysts reported by Schrock. R. R. (U.S. Pat. Nos. 4,681,956 and 4,727,215) have been shown to homogeneously metathesize at least 250 equivalents of methyl oleate. Though the reported molybdenum and tungsten catalysts can metathesize ordinary olefins (hydrocarbon chains) in good yield, they are limited in their usefulness as metathesis catalyst for functionalized olefins due to their reactivity with the functional groups.

Several rhenium alkylidene complexes have also been reported (Edwards, D. S. et al., *Organometallics* 2:1505 (1983); Edwards. D. S., "Synthesis and Reactivity of Rhenium (VII) Neopentylidene and Neopentylidyne Complexes", MIT Doctoral Thesis (1983); Horton. A. D. et al., *Organometallics* 6:893 (1987); Horton, A. D. and R. R. Schrock, *Polyhedron* 7:1841 (1988), Cai, S. et al., *J. Am Chem. Commun.*, 1489 (1988). In particular, the Edwards references describe three rhenium complexes represented by the formula Re(C-t-Bu)(CH-t-Bu)(R)$_2$ where R is a t-butoxide, trimethylsiloxide or neopentyl moiety. However, none of the previously reported rhenium compounds showed any confirmable metathesis activity in the absence of a co-catalyst or activator compound, even toward strained cyclic olefins, such as norbornene.

Heterogeneous rhenium catalysts (Re$_2$O$_7$ deposited on silica and/or alumina mixtures) have been shown to metathesize methyl oleate but for a limited duration before becoming inactive.

It would, therefore, be desirable to provide a homogeneous rhenium catalyst for metathesizing olefins, particularly functionalized olefins, at a molecular level which would be highly active, longer-lived than heterogeneous rhenium catalysts and tolerant of olefin functionalities.

SUMMARY OF THE INVENTION

This invention pertains to four-coordinate rhenium (VII) compounds and to methods for synthesizing such compounds. The rhenium compounds comprise a rhenium (VII) atom centrally linked to an alkylidene ligand, an alkylidyne ligand and two other ligands of which at least one ligand is sufficiently electron withdrawing to render the rhenium atom electrophilic enough for metathesis reactions. Preferably, the electron withdrawing ligands are alkoxide groups.

These four-coordinate compounds are well-defined, homogeneous and isolable and can be used to catalyze the metathesis of ordinary (hydrocarbon chain) and functionalized olefins in the absence of a co-catalyst or activator compound. The homogenous compounds can also catalyze the polymerization of acetylenes and ring-opening oligomerization or polymerization of cyclic olefins, such as norbornene. The compounds can also be used to make other metathesis catalyst that would otherwise be difficult to synthesize.

DETAILED DESCRIPTION OF THE INVENTION

Four-coordinate rhenium (VII) compounds of this invention can be represented by Formula I:

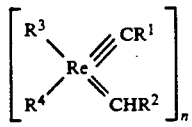

wherein $R^1$ is selected from the group consisting of an alkyl having 1 to 20 carbon atoms, an aryl having 6 to 20 carbon atoms, an aralkyl having 7 to 30 carbon atoms, halogen substituted derivative of each and silicon-containing analogs of each; $R^2$ is selected from the group consisting of $R^1$ or is a substituent resulting from the reaction of the Re=CHR$^2$ moiety of the compound with an olefin that is being metathesized; $R^3$ and $R^4$ are individually selected from groups consisting of $R^1$, a halogen, triflate, and concatenated combinations of $R^3$ and $R^4$, wherein $R^3$ and $R^4$ individually may contain alkoxide oxygen atoms which are bound to the rhenium atom; n is a positive integer (preferably one or two); and provided that when $R^1$ and $R^2$ are t-butyl and $R^3$ and $R^4$ are the same, then $R^3$ and $R^4$ are groups other than t-butoxide, trimethylsiloxide, neo-pentyl or a halogen.

Rhenium compounds of the above formula are four coordinate compounds having a rhenium (VII) atom which is centrally linked to four coordinating ligands. Centrally linked is intended to mean that the rhenium atom is central to and attached to each of these ligands. The four-coordinate compounds are characterized as having both alkylidyne (Re≡CR$^1$) and alkylidene (Re=CHR$^2$) ligands. The alkylidyne ligand is relatively inactive while the alkylidene ligand plays an integral role in the metathesis reaction and will be described in more detail below. Examples of R$^1$ and R$^2$ include but are not limited to phenyl, t-butyl, 1-methyl-1-phenyl-ethyl, trimethylsilyl, triphenylmethyl, triphenylsilyl, tri-t-butyl, tri-t-butylsilyl, 2,6,-diisopropylphenyl, 2,4,6-triisopropylphenyl and 2,6-dimethylphenyl.

The remaining two ligands (R$^3$ and R$^4$) can be any substituent which is sufficiently electron withdrawing enough to render the complex active (i.e., render the rhenium atom sufficiently electrophilic) for metathesis reactions. While it is preferable that both ligands are electron withdrawing, the compounds of this invention may contain only one electron withdrawing ligand which is sufficiently strong enough to render the complex active for metathesis. A metathesis catalyst having significant metathesis activity is one that can effect the metathesis of an ordinary or functionalized olefin at room temperature at a rate of at least one turnover per hour, in the absence of a co-catalyst or activator compound.

The activity of the catalyst can be regulated by the nature of the electron withdrawing ligands. For instance, an increase in catalytic activity can be achieved using a ligand which is strongly electron withdrawing. Preferably, R$^3$ and R$^4$ are both alkoxide ligands in which the alcohol corresponding to the electron withdrawing alkoxide ligands should have a pKa of about 9 or below. Suitable electron withdrawing ligands which fall within this range include phenoxide, hexafluoro-t-butoxide and diisopropylphenoxide. Other examples of preferred electron withdrawing ligands include alkoxides containing 2,6-dimethylphenyl, 2,4,6-trimethylphenyl, 2,6,-diisopropylphenyl, pentafluoro-phenyl, 1-methyl-1-phenyl-ethyl, 2,6-dichlorophenyl, perchlorophenyl, triphenylmethyl, triphenylsilyl, tri-t-butylsilyl, perfluoro-2-methyl-2-pentyl trifluoro-t-butyl (CF$_3$(CH$_3$)$_2$C), hexafluoro t-butyl ((CF$_3$)$_2$CH$_3$C) and perfluoro-t-butyl. Examples of concatenated R$^3$ and R$^4$ groups are pinacolate, 2,6-dimethyl-2,6-heptanediolate and propan-1 3-diolate.

Rhenium compounds of Formula I are typically monomers. However, they can form dimers, oligomers or polymers if the R$^3$ and/or R$^4$ substituents are small enough to permit bridging of two or more metal centers. This is commonly observed when the ligands are halogen atoms or small alkoxides. These compounds can be converted to monomeric rhenium compounds by substituting the bridging ligands with alkoxide or alkyl ligands. The substituted alkoxide or alkyl liands should be of a sufficient size to cause the bridge between two or more rhenium compounds to break. Some examples of these rhenium compounds include the following where t-Bu represents t-butyl:
[Re(C-t-Bu)(CH-t-Bu)Cl$_2$]$_2$
[Re(C-t-Bu)(CH-t-Bu)(2,6-dimethylaniline)Cl$_2$]$_2$
[Re(C-t-Bu)(CH-t-Bu)I$_2$]$_2$.

Complexes of this invention can optionally have one or more (preferably one or two) electron donor ligands bound to the rhenium atom. The donor ligands can be ethers (e.g. diethyl ether, tetrahydrofuran, 1,2-dimethoxyethane, 1,4-dioxane), nitrogen-containing bases (e.g. pyridine, quinuclidine, t-butylamine, 2,6-dimethylaniline), and phosphorus-containing bases (e.g. tri-phenylphosphine, dimethylphenylphosphine). The resulting complex is often isolable in the crystalline state. In solution, however, most donor ligands are lost spontaneously, or are displaced readily by one or more olefins that are being metathesized and, therefore, do not prevent the metathesis reaction.

In a preferred embodiment, the compounds of the invention are represented by Formula II:

   II where R$^1$, R$^2$ and R$^3$ are defined above. Examples of some particularly preferred bis-alkoxide rhenium compounds of Formula II include the following where t-Bu represents t-butyl:
Re(C-t-Bu)(CH-t-Bu)(2,6-diisopropylphenoxde)$_2$
Re(C-t-Bu)(CH-t-Bu)(ortho-t-butylphenoxide)$_2$
Re(C-t-Bu)(CH-t-Bu)(trifluoro-t-butoxide)$_2$
Re(C-t-Bu)(CH-t-Bu)(hexafluoro-t-butoxide)$_2$
Re(C-t-Bu)(CH-t-Bu)(2,6-dimethylphenoxide)$_2$.

The rhenium compounds of this invention can be used as catalysts for the metathesis of ordinary olefins (hydrocarbon chain) and functionalized olefins in a homogeneous phase. They can be utilized as homogeneous catalysts or can be attached covalently to inorganic (e.g. silica) or organic (e.g. polystyrene) supports to yield analogous heterogeneous catalysts. They can also function as catalysts for polymerization of acetylenes and ring-opening metathesis oligomerization or polymerization of cyclic olefins, such as norbornene. Since they are readily active compounds, they can catalyze metathesis of olefins in the absence of a co-catalyst or activator compound, such as Me$_3$SiI or Lewis acids.

According to the invention, an olefin can be metathesized by contacting it with a homogeneous rhenium metathesis catalyst in a suitable solvent, under conditions sufficient to metathesize the olefin and produce one or more metathesis products. The products can then be recovered using known separation techniques or can be further metathesized.

The metathesis reaction proceeds by addition of an olefin to the rhenium-carbon double bond (Re=CHR$^2$, a rhenium-alkylidene moiety) to form a metallacyclobutane ring (as shown below) which then releases an olefin to form a new metal-alkylidene moiety derived from the olefin. Since the Re=CHR$^2$ moiety of the complex is intimately involved in the catalytic reaction, the CHR$^2$ ligand is replaced by any other alkylidene fragment from the olefins that are being metathesized. As a result of this exchange in the alkylidene group, one can use the methods of this invention to produce rhenium catalysts having alkylidene groups which are otherwise difficult to synthesize.

Metallacyclobutane complexes which are intermediates in the metathesis reaction can also be utilized as metathesis catalysts and as catalysts for the oligomerization of acetylenes. The simplest metallacyclobutane intermediate is represented by Formula III.

   III

During a metathesis reaction, the intermediates are in equilibrium with the alkylidene complex and the free olefin as depicted in Equation 2.

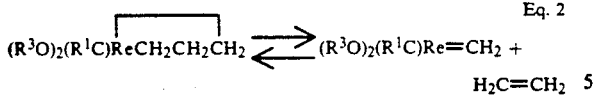

Eq. 2

The position of the equilibrium in Equation 2 will depend upon the donor ability of the solvent medium, and in the more general case where alkyl or functionalized substituents are present in the metallacyclobutane and alkylidene complexes, upon the electronic and steric properties of those substituents.

The rhenium compounds of this invention can be synthesized by reacting a compound of the formula $Re(NAr)_2(CH_2R^1)(CHR^2)$ where Ar is selected from the group consisting of 2,6-dimethylphenyl, 2,6-dichlorophenyl and diisopropylphenyl, with HCl in a suitable solvent under conditions sufficient to produce $[Re(CR^1)(CHR^2)(H_2NAr)Cl_2]_2$. However, when Ar is diisopropylphenyl, the product of this reaction is a monomer. When $R^1$ and $R^2$ are both t-butyl, the starting compound can be prepared by the sequence of reactions as described in the literature (Horton, A. D. and R. R. Schrock, *Polyhedron* 7:1841 (1988)). Other starting materials can be synthesized according to the methods described in Examples 1-3. The resulting compound is then reacted with a rigid chelating diamine in a suitable solvent under conditions sufficient to produce $Re(CR^1)(CHR^2)(Y)Cl_2$, where Y represents the diamine. Preferably, the diamine is phenylenediamine or 1,8-diaminonaphthalene. However, any rigid chelating diamine will react with the rhenium complex to produce the desired product. The product is then reacted with HCl gas under conditions sufficient to yield $[Re(CR^1)(CHR^2)Cl_2]_n$. This complex is further reacted with a sodium, lithium or potassium salt of an alkoxide under conditions sufficient to produce the rhenium catalyst. The electron withdrawing nature of the alkoxide should be sufficient enough to render the rhenium atom active for metathesis.

An alternative method for synthesizing several rhenium compounds of this invention can be performed by reacting compounds of Formula II with excess HCl or HI to produce the dihalide, $[Re(CR^1)(CHR^2)X_2]_n$, where X represents a halogen atom, such as chlorine or iodine. The resulting compound can be used as a precursor compound for preparing other rhenium compounds of Formula II by reacting the dihalide with a sodium, lithium or potassium salt of an alkoxide under conditions sufficient to produce the desired rhenium catalyst. Preferably, the starting rhenium compounds have $OR^3$ ligands, such as t-butoxide and trimethylsiloxide. When neophyl analogs are used, the reaction can be performed in dimethoxyethane (dme) to form the product $Re(CR^1)(CHR^2)X_2(dme)$ which can subsequently be used to produce the desired rhenium compound as previously described.

A typical synthesis is illustrated by the sequence of reactions shown in Equations 3, 7-9. An alternative synthesis is represented by Equations 3-6. These reactions can be performed in suitable solvents (e.g., dimethoxyethane, methylene chloride, pentane, toluene, tetrahydrofuran (THF), or dichloromethane) and at a temperature range of from about −78° C. to about 25° C. The synthesized products are recovered by filtering the reaction mixture and removing all solvents and readily volatile products from the filtrate in vacuo.

In the following equations below, t-Bu=t-butyl, Me=methyl, Ar=2,6-dimethylphenyl, OTf-=OSO$_2$CF$_3$, pda=1,2-phenylenediamine and $R^3$ is previously defined.

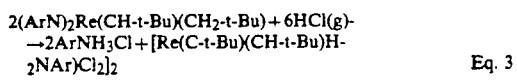

Eq. 3

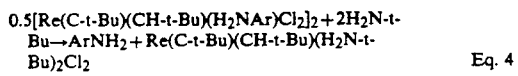

Eq. 4

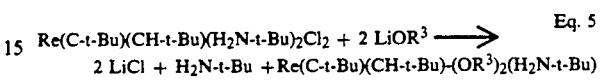

Eq. 5

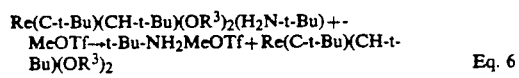

Eq. 6

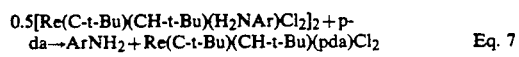

Eq. 7

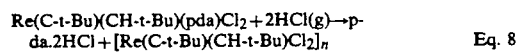

Eq. 8

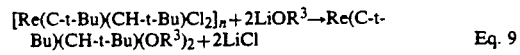

Eq. 9

This invention is further illustrated by the following non-limiting examples.

In order to avoid the presence of oxygen and moisture, the latter being especially destructive, the following examples were carried out in an atmosphere of dry molecular nitrogen using dry, pure solvents. Several of the pure, isolated products, however, are stable to oxygen and water for extended periods (several weeks).

In the examples below, t-Bu=t-butyl, Me=methyl, Ar=2,6-dimethylphenyl, OAr'=2,6-diisopropylphenoxide, pda=1,2-phenylenediamine, py=pyridine and OTf=OSO$_2$CF$_3$.

EXAMPLE 1

Preparation of Re(NAr)$_2$Cl$_3$py

To a stirring suspension of Re$_2$O$_7$ (1.0 g, 2.07 mmol) in 50 ml methylene chloride was added sequentially 2,6-dimethylaniline (1,84 ml, 12.4 mmol) and pyridine (3.05 ml. 78 mmol) resulting in a dark red solution. Chlorotrimethylsilane (4.8 ml, 38 mmol) was then added, the solution darkened and all solids dissolved after 20 minutes. The reaction was stirred at room temperature two hours and then the dark green solution was reduced to dryness. The solids were extracted with boiling benzene and filtered through Celite ™ (hydrated diatomaceous amorphous silica). Concentration of the filtrate and addition of pentane afforded Re(NAr)$_2$Cl$_3$py as a dark green crystalline solid (2.2 g. 86%) whose $^1$H NMR was identical to a compound previously reported by Horton, A. D. and R. R. Schrock, *Polyhedron* 7:1841 (1988).

A similar method can be used to produce Re(2,6-diisopropylaniline)$_2$Cl$_3$py where 2,6-diisopropylimido is added in place of 2,6-dimethylaniline.

EXAMPLE 2

Preparation of Re(N-t-Bu)$_2$Cl$_3$

To a stirring suspension of Re$_2$O$_7$ (4.0 g, 8.26 mmol) in methylene chloride at 0° C. was added chlorotrimethylsilane (14.8 ml. 115 mmol) and then t-butylamine (17.4 ml, 165 mmol) was added quickly dropwise. The solution instantly turned bright yellow and a white precipitate containing $Me_3CNH_3Cl$ formed. After stirring the solution of crude $Re(N-t-Bu)_3-(OSiMe_3)$ for 20 minutes at room temperature, excess HCl(g) was bubbled through the solution. The resulting dark orange solution was then filtered and the filtrate reduced to dryness and extracted with ether. The ether extracts were then concentrated and cooled to afford large orange crystals of $Re(N-t-Bu)_2Cl_3$ (5.7 g, 79%) whose $^1H$ NMR was identical with that previously reported by Edwards, D. S. et al., *Organometallics* 2:1505–1513 (1983).

EXAMPLE 3

Preparation of $[Re(C-t-Bu)(CH-t-Bu)(H_2NAr)Cl_2]_2$

A solution of $Re(NAr)_2(CH-t-Bu)(CH_2-t-Bu)$ (4.64 g, 8.2 mmol) (Horton. A. D. and R. R. Schrock. *Polyhedron* 7:1841 (1988)) in dimethoxyethane was cooled to 0° C. and treated with HCl(g) (590 ml. 26 mmol). The orange solution immediately darkened and a white precipitate was observed. After stirring at 25° C. for 2.5 hours, the solvent was removed in vacuo leaving a beige powder that was extracted away from insoluble $ArNH_3Cl$ with benzene and filtered through a pad of Celite TM. The filtrate was then reduced to dryness in vacuo and washed with pentane to yield a faintly orange powder (3.4 g. 80% yield).

Anal. Calcd for $Re_2C_{36}H_{60}Cl_4N_2$: C. 41.77; H, 5.84; N, 2.71. Found: C. 42.11; H, 6.00; N, 2.50.

Partial $^1H$ NMR $(C_6D_6)$ (The compound exists as two isomers) $\delta$14.49. 14.48 (s, 4, C$\underline{H}$CMe$_3$), 2.37, 2.32, 2.28, 2.17 (s. 6 each, 2,6-$\underline{Me_2}$-$C_6H_3$), 1.39, 1.38, 1.08 1.01 (s, 18 each, C$\underline{Me}_3$). Partial $^{13}C$(THF-$d_8$, major isomer) $\delta$292.1 ($\underline{C}$CMe$_3$), 286.3 ($\underline{C}$HCMe$_3$, $J_{CH}$=130 Hz), 31.5. 28.5 (C$\underline{Me}_3$).

EXAMPLE 4

Preparation of $Re(C-t-Bu)(CH-t-Bu)(H_2N-t-Bu)_2Cl_2$

To an orange solution of $[Re(C-t-Bu)(CH-t-Bu)-(H_2NAr)Cl_2]_2$ (0.5 g, 0.48 mmol) in tetrahydrofuran was added t-butylamine (1.0 ml). The reaction mixture was stirred for twelve hours at room temperature. The solution was then reduced in volume to 5 ml and pentane was added, causing the product to crystallize from the reaction mixture as fine silky needles. (0.49 g. 93% yield). The product may also be prepared in the same fashion by adding t-butylamine directly to the crude reaction product in Example 3.

$^1H$ NMR $(CD_2Cl_2)$ $\delta$14.52 (s, 1, C$\underline{H}$CMe$_3$), 4.63, 4.23 (d, 2 each, N$\underline{H}_2$CMe$_3$), 1.40, 1.36 (s, each 9, C$\underline{Me}_3$), 1.18 (s, 18, H$_2$NC$\underline{Me}_3$). Partial $^{13}C$ NMR $(CD_2Cl_2, -60°$ C.) $\delta$298.6 ($\underline{C}$HCMe$_3$, $J_{CH}$=131 Hz). 286.2 ($\underline{C}$CMe$_3$), 29.5 (NH$_2$C$\underline{Me}_3$), 28.8, 31.0 (C$\underline{Me}_3$).

EXAMPLE 5

Preparation of $Re(C-t-Bu)(CH-t-Bu)(OAr')_2(H_2N-t-Bu)$

To a $-40°$ C. solution of $Re(C-t-Bu)(CH-t-Bu)(H_2N-t-Bu)_2Cl_2$ (2.0 g, 3.7 mmol) in $CH_2Cl_2$ was added solid lithium 2,6-diisopropylphenoxide monoetherate (1.9 g, 7.4 mmol). The orange solution gradually became bright yellow and was stirred at room temperature for 40 minutes. The volatiles were then removed in vacuo and the solid residue extracted with pentane. The pentane extract was filtered through a pad of Celite TM. Concentration and cooling of the filtrate yielded large yellow cubes (2.0 g, yield=73%). Partial $^1H$ NMR $(C_6D_6$, varies with concentration) $\delta$11.15 (s, 1, C$\underline{H}$CMe$_3$), 3.41 (sept, 4 C$\underline{H}$Me$_2$), 1,48, 0.56 (s, 9 each, C$\underline{Me}_3$). Partial $^{13}C$ NMR $(CD_2Cl_2, -60°$ C.) $\delta$293.1 ($\underline{C}$CMe$_3$), 234.4 ($\underline{C}$HCMe$_3$, $J_{CH}$=123 Hz), 51.6, 50.8, 43.9 (C$\underline{Me}_3$).

EXAMPLE 6

Preparation of $Re(C-t-Bu)(CH-t-Bu)(OAr')_2$

To a solution of $Re(C-t-Bu)(OAr')_2(H_2N-t-Bu)$ (25 mg. 0.033 mmol) in $C_6D_6$ (c.a. 700 μl) was added (via syringe) methyl triflate (3.8 μl, 0.033 mmol). A white precipitate formed within a few minutes and was removed by filtration. The $^1H$ NMR indicated a quantitative yield of $Re(CCMe_3)(CHCMe_3)(OAr')_2$. This complex was stable in solution indefinitely, but was not stable in the solid state. This complex is typically generated in situ for further reactions. Partial $^1H$ $(C_6D_6)$ $\delta$ 10.72 (s, 1, C$\underline{H}$CMe$_3$), 3.56 (sept, 4, C$\underline{H}$Me$_2$), 1.19, 0 99 (s, 9 each, C$\underline{Me}_3$). Partial $^{13}C(C_6D_6)$ $\delta$293.6 ($\underline{C}$CMe$_3$), 240.1 ($\underline{C}$HCMe$_3$, $J_{CH}$=125 Hz), 27.9, 23.6 (C$\underline{Me}_3$).

EXAMPLE 7

Preparation of $Re(C-t-Bu)(CH-t-Bu)(pda)Cl_2$

To solution of $[Re(C-t-Bu)(CH-t-Bu)(H_2NAr)Cl_2]_2$ (1.5 g, 1,45 mmol) in tetrahydrofuran (THF) was added solid 1,2-phenylenediamine (0.32 g, 2.9 mmol). The solution was stirred at room temperature 25 minutes and the solvent removed in vacuo. The solid residue was washed with pentane and then twice reprecipitated from THF/pentane to remove residual aniline. A pale orange product was obtained in 95% yield (1.39 g). Partial $^1H$ NMR $(C_6D_6)$ $\delta$13.42 (s, 1, C$\underline{H}$CMe$_3$), 1.62, 1.36 (s, 9 each, C$\underline{Me}_3$). Partial $^{13}C$ $(CD_2Cl_2)$ $\delta$295.6 ($\underline{C}$CMe$_3$) 292.0 ($\underline{C}$HCMe$_3$, $J_{CH}$=118 Hz), 31.2, 28.1 (C$\underline{Me}_3$).

EXAMPLE 8

Preparation of $[Re(C-t-Bu)(CH-t-Bu)Cl_2]_n$

Addition of HCl(g) (98 ml, 4.4 mol) via syringe to a dimethoxyethane solution of $Re(C-t-Bu)(CH-t-Bu)(p-da)-Cl_2$ (1.0 g. 1.98 mmol) resulted in the immediate formation of a white precipitate at room temperature. After 20 minutes, the precipitate was removed by filtration and the orange filtrate reduced to dryness. The resulting solid was washed with pentane to yield a pale orange powder (0.67 g. 85%) that was insoluble in all but strongly coordinating solvents. $^1H$ NMR (THF-$d_8$) $\delta$13.26 (s, 1, C$\underline{H}$CMe$_3$), 1.35, 1.26 (s, 9, C$\underline{Me}_3$). Partial $^{13}C$ NMR (THF-$d_8$) $\delta$239.9 ($\underline{C}$CMe$_3$), 285.8 ($\underline{C}$HCMe$_3$, $J_{CH}$=125 Hz), 31.4, 28.4 (C$\underline{Me}_3$).

EXAMPLE 9

Preparation of $Re(C-t-Bu)(CH-t-Bu)(OC(CF_3)_2CH_3)_2$

To a $-40°$ C. THF solution of $[Re(C-t-Bu)(CH-t-Bu)-Cl_2]_n$ (250 mg. 0.63 mmol) was added solid potassium hexafluoro-t-butoxide (277 mg, 1.26 mmol). The orange solution darkened as it was stirred at room temperature for 45 minutes. The solvent was then removed in vacuo and the residue extracted with pentane and filtered through a pad of Celite TM. The resulting orange solution was reduced to dryness, quantitatively yielding $Re(C-t-Bu)(CH-t-Bu)(OC(CF_3)_2CH_3)_2$ as an orange oil. Partial $^1H$ NMR $(C_6D_6)$ $\delta$11.08 (s, 1, C$\underline{H}$Me$_3$), 1.15, 1.13 (s, C$\underline{Me}_3$). Partial $^{13}C$ NMR $(C_6D_6)$ δ295.8 (CCMe₃), 248.8 (CHCMe₃, $J_{CH}$=127 Hz), 31.9, 29.9 (CMe₃).

EXAMPLE 10

Metathesis of cis-2-pentene

To 35 mg Re(C-t-Bu)(CH-t-Bu)(OC(CF₃)₂CH₃)₂ (0.05 mmol) in 5 ml of benzene was added 100 equivalents of cis-2-pentene (546 µl, 5 mmol). After 150 minutes, gas chromatography (GC) analysis showed an approximately 1:2:1 mixture of 2-butenes, 2-pentenes and 3-hexenes. An additional 100 equivalents of cis-2-pentene (546 µl, 5 mmol) were then added and equilibrium was reestablished in less than 30 minutes. A ¹H NMR study of the reaction of Re(C-t-Bu)(CH t-Bu)(OC(CF₃)₂CH₃)₂ and 10 equivalents cis-2-pentene showed the presence of propagating ethylidene and propylidene species even after two days in solution.

EXAMPLE 11

Metathesis of Methyl Oleate

To 20 mg [Re(C-t-Bu)(CH-t-Bu)Cl₂]ₙ (0.05 mmol) as a suspension in 5 ml CH₂Cl₂ was added solid potassium hexafluoro-t-butoxide (22 mg, 0.10 mmol). After 30 minutes all the solids had dissolved to yield a yellow solution, and an internal standard of mesitylene and 50 equivalents of methyl oleate (850 µl, 1. 2.5 mmol) were added. After 12 hours, the equilibrium (~1:2:1) between Me(CH₂)₇CH=CH(CH₂)₇Me, Me(CH₂)₇CH=CH(CH₂)₇CO₂Me and MeO₂C(CH₂)₇CH=CH(CH₂)₇CO₂Me was established. The catalyst solution was then allowed to stand undisturbed for 24 hours and then an additional 50 equivalents methyl oleate (850 µl, 2.5 mmol) were added. Equilibrium was reestablished after 7.5 hours. The products of the metathesis were identified by comparison with authentic GC traces. The activity of this catalyst is at least 200 equivalents of methyl oleate and the catalytic solutions are stable for at least three days.

EXAMPLE 12

Metathesis of Methyl Oleate Accelerated by Initial Reaction with 3-Hexene

To 15 mg [Re(C-t-Bu)(CH-t-Bu)Cl₂]ₙ (0.038 mmol) as a suspension in 2 ml CH₂Cl₂ was added solid potassium hexafluoro-t-butoxide (17 mg, 0.076 mmol). After 30 minutes, the solution was clear yellow and 10 equivalents of cis-3-hexene (47 µl, 0.38 mmol) were added. After stirring for 7 hours, 3 ml CH₂Cl₂, an internal standard of 1-phenyloctane and 50 equivalents of methyl oleate (640 µl, 1.9 mmol) were added. Equilibrium was established after 150 minutes, and then an additional 100 equivalents of methyl oleate (1280 µl, 3.8 mmol) were added. After six hours at room temperature, equilibrium (~1:2:1) was again achieved.

EQUIVALENTS

Those skilled in the art will recognize, or be able to ascertain employing no more than routine experimentation, many equivalents to the specific embodiments of the invention described herein. Such equivalents are intended to be encompassed by the following claims.

We claim:

1. A homogeneous rhenium metathesis catalyst, comprising a rhenium (VII) atom centrally linked to an alkylidene ligand, an alkylidyne ligand, and two other ligands of which at least one ligand is an electron withdrawing ligand in which its corresponding free ligand in protinated form has a pKa below about 9; wherein the catalyst has significant metathesis activity that can effect the metathesis of an ordinary or functionalized olefin at room temperature at a rate of at least one turnover per hour.

2. The catalyst of claim 1, wherein the electron withdrawing ligand is an alkoxide in which its corresponding alcohol has a pKa below about 9.

3. The catalyst of claim 2, wherein the electron withdrawing ligand is selected from the group consisting of alkoxides containing 2,6-dimethylphenyl, 2,4,6-trimethylphenyl, 2,6-diisopropylphenyl, pentafluorophenyl, 2,6-dichlorophenyl, perchlorophenyl, triphenylmethyl, triphenylsilyl, tri-t-butylsilyl, perfluoro-2-methyl-2-pentyl, trifluoro-t-butyl, hexafluoro-t-butyl, perfluoro-t-butyl, pinacolate, 2,6-dimethyl—2,6-heptane-diolate and propan-1,3-diolate.

4. A compound of the formula:

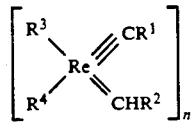

wherein
R¹ is selected from the group consisting of an alkyl having 1 to 20 carbon atoms, an aryl having 6 to 20 carbon atoms, an aralkyl having 7 to 30 carbon atoms, halogen substituted derivative of each and silicon-containing analogs of each;

R² is selected from the group consisting of R¹ or is a substituent resulting from the reaction of the Re=CHR² moiety of the compound with an olefin that is being metathesized;

R³ and R⁴ are individually selected from groups consisting of R¹, a halogen, triflate, and concatenated combinations of R³ and R⁴; wherein R³ and R⁴ individually may contain alkoxide oxygen atoms which are bound to the rhenium atom;

n is a positive integer; and provided that when R¹ and R² are t-butyl and R³ and R⁴ are the same, then R³ and R⁴ are groups other than t-butoxide, trimethylsiloxide, neopentyl or a halogen.

5. The compound of claim 4, wherein R¹ and R² are individually selected from the group consisting of phenyl, 2,6-diisopropylphenyl, 2,4,6-triisopropyl-phenyl, t-butyl, trimethylsilyl, triphenylmethyl, triphenylsilyl, tri-t-butyl, tri-t-butylsilyl, 1-methyl-1-phenyl ethyl and 2,6-dimethylphenyl.

6. The compound of claim 5, wherein R³ and R⁴ are individually selected from the group consisting of alkoxides containing 2,6-dimethylphenyl, 2,4,6-trimethylphenyl, 2,6-diisopropylphenyl, pentafluorophenyl, 2,6-dichlorophenyl, perchlorophenyl, triphenylmethyl, triphenylsilyl, tri-t-butylsilyl, perfluoro-2-methyl-2-pentyl, trifluoro-t-butyl, hexafluoro-t-butyl, perfluoro-t-butyl, pinacolate, 2,6-dimethyl-2,6-heptanediolate and propan-1,3-diolate.

7. The compound of claim 4, further comprising an electron donor ligand bound to Re, selected from the group consisting of an ether, a nitrogen-containing base and a phosphorus-containing base.

8. The compound of claim 7, wherein the donor ligand is selected from the group consisting of diethyl ether, tetrahydrofuran, 1,2-dimethoxyethane, 1,4-dioxane, pyridine, quinuclidine, t-butylamine, 2,6-dimethylaniline, triphenylphosphine and dimethylphenylphosphine.

9. A compound of the formula:

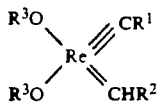

wherein $R^1$, $R^2$ and $R^3$ are individually selected from the group consisting of an alkyl having one to 20 carbon atoms, an aryl having six to 20 carbon atoms, an aralkyl having seven to 30 carbon atoms, halogen substituted derivative thereof and silicon-containing analogs thereof; and $R^2$ further consists of a substituent resulting from the reaction of the Re=$CHR^2$ moiety of the compound with an olefin that is being metathesized, provided that when $R^1$ and $R^2$ are t-butyl, then $R^3$ is a group other than t-butyl or trimethylsilyl.

10. The compound of claim 9, wherein $R^1$ and $R^2$ are individually selected from the group consisting of phenyl, 2,6-diisopropylphenyl, 2,4,6-triisopropyl-phenyl, t-butyl, trimethylsilyl, triphenylmethyl, triphenylsilyl, tri-t-butyl, tri-t-butylsilyl, 1-methyl-1-phenyl ethyl and 2,6-dimethylphenyl.

11. The compound of claim 10, wherein $R^3$ is selected from the group consisting of 2,6-dimethylphenyl, 2,4,6-trimethylphenyl, 2,6-diisopropylphenyl, pentafluorophenyl, 2,6-dichlorophenyl, perchlorophenyl, triphenylmethyl, triphenylsilyl, tri-t-butylsilyl, perfluoro-2-methyl-2-pentyl, trifluoro-t-butyl, hexafluoro-t-butyl, perfluoro-t-butyl, 2,3-dimethylbutdiyl, 2,6-dimethyl-2,6-heptanediyl and propan-1,3-diyl.

12. The compound of claim 9, wherein $R^1$ and $R^2$ are t-butyl or 1-methyl-1-phenyl-ethyl and $R^3$ is diisopropylphenyl.

13. The compound of claim 9, wherein $R^1$ and $R^2$ are t-butyl or 1-methyl-1-phenyl-ethyl and $R^3$ is dimethylphenyl.

14. The compound of claim 9, wherein $R^1$ and $R^2$ are t-butyl or 1-methyl-1-phenyl-ethyl and $R^3$ is ortho-t-butylphenyl.

15. The compound of claim 9, wherein $R^1$ and $R^2$ are t-butyl or 1-methyl-1-phenyl-ethyl and $R^3$ is trifluoro-t-butyl or hexafluoro-t-butyl.

16. A method for preparing a homogeneous rhenium catalyst of the formula:

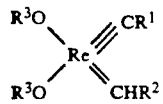

wherein $R^1$, $R^2$ and $R^3$ are individually selected from the group consisting of an alkyl having one to 20 carbon atoms, an aryl having six to 20 carbon atoms, an aralkyl having seven to 30 carbon atoms, halogen substituted derivative thereof and silicon-containing analogs thereof; and $R^2$ further consists of a substituent resulting from the reaction of the Re=$CHR^2$ moiety of the compound with an olefin that is being metathesized, comprising the steps of:
a) reacting a compound of the formula Re(NAr)$_2$(CH$_2$R$^1$)(CHR$^2$) where Ar is selected from the group consisting of 2,6-dimethylphenyl, 2,6-dichlorophenyl and diisopropylphenyl, with HCl in a suitable solvent under conditions sufficient to produce [Re(CR$^1$)(CHR$^2$)(H$_2$NAr)Cl$_2$]$_2$; wherein when Ar is diisopropylphenyl, then the product is a monomer;
b) reacting the product of step (a) with a rigid chelating diamine in a suitable solvent under conditions sufficient to produce Re(CR$^1$)(CHR$^2$)(Y)Cl$_2$, where Y is the diamine;
c) reacting the product of step (b) with HCl gas under conditions sufficient to yield [Re(CR$^1$)(CHR$^2$)Cl$_2$]$_n$, where n is a positive integer; and
d) reacting the product of step (c) with a sodium, lithium or potassium salt of an alkoxide under conditions sufficient to produce the rhenium catalyst.

17. A method for preparing a homogeneous rhenium catalyst of the formula:

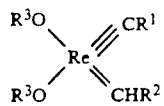

wherein $R^1$, $R^2$ and $R^3$ are individually selected from the group consisting of an alkyl having one to 20 carbon atoms, an aryl having six to 20 carbon atoms, an aralkyl having seven to 30 carbon atoms, halogen substituted derivative thereof and silicon-containing analogs thereof; and $R^2$ further consists of a substituent resulting from the reaction of the Re=$CHR^2$ moiety of the compound with an olefin that is being metathesized, comprising the steps of:
a) reacting a compound of the formula Re(CR$^1$)(CHR$^2$)(OR$^3$) with HCl in a suitable solvent under conditions sufficient to produce [Re(CR$^1$)(CHR$^2$)Cl$_2$]$_n$, wherein n is a positive integer; and
b) reacting the product of step (a) with a sodium, lithium or potassium salt of an alkoxide under conditions sufficient to produce a rhenium catalyst having different OR$^3$ ligands than the starting compound.

* * * * *